US006187339B1

(12) United States Patent
de Haan et al.

(10) Patent No.: US 6,187,339 B1
(45) Date of Patent: *Feb. 13, 2001

(54) SOLID PHARMACEUTICAL COMPOSITION COMPRISING AN EXCIPIENT CAPABLE OF BINDING WATER

(75) Inventors: Pieter de Haan; Henrika Gerardina Maria Poels-Janssen, both of Oss (NL)

(73) Assignee: Akzo Nobel N.V., Arnhem (NL)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/544,042

(22) Filed: Oct. 17, 1995

(30) Foreign Application Priority Data

Oct. 17, 1994 (EP) ................................. 94203017

(51) Int. Cl.[7] .................................. A61K 47/30
(52) U.S. Cl. .................. 424/469; 424/451; 424/452; 424/464; 424/465; 424/488; 514/170; 514/781; 514/970
(58) Field of Search .................... 424/469, 451, 424/452, 461, 464, 465, 484, 488, 494, 497; 514/170, 177, 182, 781, 970

(56) References Cited

U.S. PATENT DOCUMENTS

| | | | |
|---|---|---|---|
| 2,965,541 | * 12/1960 | Byrnes | 424/471 |
| 3,568,828 | * 3/1971 | Lerner | 206/528 |
| 4,544,554 | * 10/1985 | Pasquale | 514/170 |
| 4,661,647 | * 4/1987 | Serpelloni et al. | 568/868 |
| 5,085,869 | * 2/1992 | Olthoff et al. | 424/499 |
| 5,169,645 | * 12/1992 | Shukla et al. | 424/499 |
| 5,382,434 | * 1/1995 | Haan et al. | 424/465 |
| 5,800,834 | * 9/1998 | Spireas et al. | 424/451 |
| 5,801,220 | * 9/1998 | Desai et al. | 524/13 |
| 5,840,769 | * 11/1998 | Kolter et al. | 514/781 |
| 6,057,139 | * 5/2000 | Kulkarni et al. | 435/188 |
| 6,096,337 | * 8/2000 | Spireas et al. | 424/451 |

FOREIGN PATENT DOCUMENTS

| | | | |
|---|---|---|---|
| 0 598 337 | * | 5/1994 | (EP) . |
| 0598337 | * | 5/1995 | (EP) . |
| WO 94/23700 | * | 10/1994 | (WO) . |
| WOA 9423700 | * | 10/1994 | (WO) . |
| WO 95/06461 | * | 3/1995 | (WO) . |

OTHER PUBLICATIONS

Kirk–Othmer. Encyclopedia of Chemical Technology, Third Edition. Size Measurement of Particles. vol. 21, pp. 106–131. (1983).*
Tan et al. Controlled Drug Release From Silicone Coated Tablets: Preliminary Evaluation of Coating Techniques and Characterization of Membrane Permeation Kinetics.*
International Journal of Pharmaceutics, vol. 42, Nos. 1–3, Mar. 1988, pp. 161–169.*
Herman et al. Modified Starches as Hydrophilic Matrices For Controlled Oral Delivery. II. In Vitro Drug Release Evaluation of Thermally Modified Starches. Intl. J. of Pharm. 56(1), pp. 65–70. (1989).*
Munoz–Ruiz et al. Tabletting Properties of New Granular Microcrystalline Celluloses. European Journal of Pharmaceutics and Biopharmaceutics. vol. 40, No. 1, pp. 36–40. (Feb. 1994).*
Size Enlargement of Particles. Kirk–Othmer Encyclopedia of Chemical Technology, Third Edition. John Wiley & Sons. N.Y. vol. 21:pp. 106–131. (1983).*

* cited by examiner

Primary Examiner—Robert H. Harrison
(74) Attorney, Agent, or Firm—William M. Blackstone

(57) ABSTRACT

The invention concerns a solid pharmaceutical composition comprising less than 7% by weight of an oil or oily substance, a low dosage active ingredient, and a water insoluble non-cross-linked polymeric excipient capable of binding water and having a mean particle size greater than 150 μm. The composition can be obtained by a simple procedure comprising mixing the water insoluble non-cross-linked polymeric excipient capable of binding water and the active ingredient, which is dissolved or dispersed in an oil or an oily substance, in an aqueous dispersion thereof, or in water.

11 Claims, No Drawings

SOLID PHARMACEUTICAL COMPOSITION COMPRISING AN EXCIPIENT CAPABLE OF BINDING WATER

The present invention concerns solid pharmaceutical compositions comprising a water insoluble non-cross-linked polymeric excipient capable of binding water and less than 7% by weight of an oil or oily substance, and a process for the preparation of said solid composition.

Many solid pharmaceutical compositions are known in the art, see for instance the standard reference work of Gennaro et al., Remington's Pharmaceutical Sciences, (18th ed., Mack Publishing Company, 1990, see especially Part 8, chapter 89: Pharmaceutical Preparations and Their Manufacture). Usually tablets or capsules are prepared from granules comprising the active ingredients and additives or excipients. These excipients include diluents, binders, glidants, lubricants, and the like. General methods of tablet preparation are the wet-granulation method, the dry-granulation method, and the direct compression method. Each of these methods has its disadvantages, especially when low dosage active ingredients are formulated. For instance, in the wet-granulation method the active ingredient is usually dissolved or dispersed in a liquid, which is frequently an organic solvent causing environmental problems. In the dry-granulation method it is extremely difficult to get acceptable content uniformity when low dosage active ingredients are used. Direct compression methods are not generally applicable, since only ingredients having all the physical requirements for the formation of a good tablet can be used, especially possessing good cohesive and flow properties. Only very few ingredients have these required properties.

Since it is of considerable advantage to increase the efficiency of tabletting operations and reduce costs by using the smallest amount of floor space and labour as possible, there is a need for a very simple method of preparing drug loaded carrier particles for use in tablets and capsules. Moreover, if low dosage active ingredients are compressed into tablets problems concerning the content uniformity can occur. Existing methods for preparing tablets with low dosage active ingredients suffer from complexity, environmental problems, or poor reproducibility. An improvement was disclosed by Vervaet et al. (Int. J. Pharmaceutics 108 (1994) 207–212), who prepared pellets from microcrystalline cellulose Avicel PH-101 and PEG-40 hydrogenated castor oil. These compositions contain 7–21% of hydrogenated castor oil and relatively small particle sized microcrystalline cellulose, and should be granulated, extruded and spheronised to obtain the pellets. Compositions comprising Avicel PH-101 were also disclosed in the intermediate PCT patent application WO 94/23700. Other methods requiring granulation are disclosed by I. Ullah et al. (Pharmaceutical Technology, September 1987, 48–54) and C-M. Chen et al. (Drug Development and Industrial Pharmacy, 16 (3), 1990, 379–394). According to these methods a moisture-activated dry granulation method was obtained by blending a drug with a dry binder, such as microcrystalline cellulose which is capable of absorbing remaining free moisture. Pharmaceutical compositions including water-swellable, but water-insoluble cross-linked polymers together with an oil, are disclosed in EP 598,337. Such compositions, however, have inadequate flow properties.

The present invention offers a solution for obtaining drug loaded carrier particles without the need of a granulation step by using a solid pharmaceutical composition comprising less than 7% by weight of an oil or oily substance, a low dosage active ingredient, and a water insoluble non-cross-linked polymeric excipient capable of binding water and having a mean particle size greater than 150 μm.

Water insoluble non-cross-linked polymeric excipients capable of binding water are diluents added to dosage units to increase the mixture and the resulting dosage units bulk. The preferred diluent in this invention is a carrier material with water uptake properties for incorporation of emulsions or oily liquids comprising a solution or dispersion of a low dose active agent. The preferred carrier materials are water insoluble cellulose or starch, like amorphous and microcrystalline cellulose or agglomerated starch, or mixtures thereof. The carrier material has a mean particle size greater than 150 μm (micrometer), and preferably at least 180 μm. The carrier material will typically make up from 20 to 99% by weight of the resulting pharmaceutical composition, which may contain apart from the carrier material capable of binding water any suitable pharmaceutically acceptable auxiliary. Auxiliaries include fillers, diluents, disintegrants, binders, colorants, lubricants, and the like. A preferred water insoluble non-cross-linked polymeric excipient capable of binding water is commercially available Avicel PH-200.

The active ingredient is processed in an oil or oily substance with preferably a melting point below 40° C. Preferably the pharmaceutical composition comprises a dosage of 0.005 to 5 percent by weight of the active ingredient.

The active ingredient can be any active ingredient, and preferably a steroid. Preferred steroidal agents are selected from progestagen, estrogen, and mixtures thereof. With more preference the progestagens are selected from desogestrel, 3-ketodesogestrel, Org 30659 (17α-17-hydroxy-11-methylene-19-norpregna-4,15-dien-20-yn-3-one), levonorgestrel, and gestodene, whereas the estrogens are selected from ethinyl estradiol (EE), estradiol, and mestranol. Usually mixtures of progestagens and estrogens are used. Most preferred are tablets comprising desogestrel or ethinyl estradiol or mixtures thereof. Other suitable active ingredients are for example levothyronine, thyroxine, digitoxine and digoxine.

Oils for dissolving or suspending the progestagen and the estrogen can be of a natural, semi-synthetic or synthetic source. Fixed oils of vegetable origin consist mainly of (mixed) glycerides. Examples are arachis oil, castor oil, sesame oil, fractionized coconut oil (miglyols), ethyl oleate, maize oil, Gelucire (partial glycerides and polyglycide fatty acids), and the like. Other suitable liquids are liquid paraffin, dimethyl silicone fluid, triacetin, mono- and di-glycerides, and esters of polyethyleneglycol, propyleneglycol, polyglycerol, glycerol, or glyceryl. The content of oil or oily substances will typically make up less than 7% by weight of the mixture for tabletting or capsulation, and preferably less than 4%, and more preferably from about 0.1 to 4%. The active compound can also be processed to mixtures of the oily substance and water. Emulsions are an example of such mixtures. If the oil content is 0% (thus no oil is present in the composition), preferably an aqueous solution or dispersion of the active ingredient is used. Known techniques and compositions for preparing suitable mixtures with the active compounds, oils, oily substances and optionally water are applicable. Emulsifying agents can be of the group of viscosity increasing agents like sugars, polyethylene glycols, gelatines, hydroxypropylcellulose (HPC), amylopectin, starch, carboxymethylcellulose (CMC), hydroxypropylmethylcellulose (HPMC), polyvinylpyrrolidone, gums like Arabic and Guar gum, cellulose based and starch based materials, and the like. Also emulsifying agents with ionogenic properties (sodium laurylsulfate, sodium dioctylsulfosuccinate, cetrimonium bromide) and nonionogenic properties [monostearine (glycerol monostearate), monoleine, sorbitan esters (Spans), PEG-sorbitan ethers (Tweens, polysorbates), PEG-fatty acid esters (like the Polyoxyl 50 stearates), PEG-fat-alcohol ethers (Cetomacrogols) and the like] can be applied for stabilizing the emulsion.

The composition and concentrations of the components of the liquids (comprising the active compound) should be as such that agglomeration during mixing with the carrier-materials is avoided. For instance, agglomeration by addition of high concentrations of emulsifying agents of the group of viscosity increasing agents results in mixtures with unacceptable flow properties. For that reason any agglomeration should be avoided. The ratio between the amount of the water insoluble polymeric excipient capable of binding water and the amount of applied water should preferable be higher than 5:1, and more preferably higher than 10:1, in order to avoid impaired flow properties on the one hand and a drying step on the other hand. Materials to improve the flow characteristics are referred to as glidants. As an example, silicon dioxide, magnesium laurylsulfate or magnesium oxide can be added to the formulation to reduce interparticulate friction and to eliminate the problem associated with the flow of materials from larger to smaller apertures in the tablet presses. The composition comprising progestagen may further comprise colouring agents, disintegrants, lubricants, excipients to modify drug-release characteristics, and other additives.

The process for the preparation of the solid pharmaceutical composition of the invention is characterized in that a low dosage of an active ingredient is dissolved or dispersed in an oil or an oily substance, in an aqueous dispersion thereof, or in water, and thereafter mixed with a water insoluble non-cross-linked polymeric excipient capable of binding water and having a mean particle size greater than 150 $\mu$m, after which the solid composition can optionally be mixed with more of the water insoluble non-cross-linked polymeric excipient capable of binding water or with any other suitable pharmaceutically acceptable auxiliary, after which the solid composition obtained can optionally be compressed into tablets or filled into capsules.

The process of this invention excels by its simplicity and safety. The active substance is preferably suspended, dispersed, emulsified, or dissolved in the oil or oily substance, after which the liquid mass is mixed in a mixer with the water insoluble non-cross-linked polymeric excipient capable of binding water. Drying is not necessary. To improve the flow properties a glidand may optionally be added, for instance silicon oxide. Usually it is not necessary to add a lubricant, and the mixture can directly be used for tabletting or making capsules. Granulation to improve flow characteristics or to improve homogeneity by reducing segregation is not necessary.

The composition of this invention has various advantages over the known compositions, i.e. simplicity of the process not requiring granulation, agglomeration, drying or mixing with lubricants, and safety of the process not requiring organic solvents and possibility of performing the process in a closed system. The stability and the content uniformity of the active ingredient in the composition of the invention is good to excellent.

Tablets and capsules can be prepared according to generally known procedures, for instance as described in the reference work Gennaro et al., Remington's Pharmaceutical Sciences, (18th ed., Mack Publishing Company, 1990, see especially Part 8: Pharmaceutical Preparations and Their Manufacture).

The invention is further illustrated by the following examples:

EXAMPLE 1

The active ingredients were processed to a homogeneous mixture (weight per tablet):

| | |
|---|---|
| desogestrel | 150 $\mu$g |
| Ethinyl estradiol (EE) | 30 $\mu$g |
| Miglyol 812 | 1.3 mg |
| Water | 3.68 mg |
| Avicel PH-200 | 58.99 mg |
| Methylcellulose MHB-50 | 0.07 mg |
| Silicon dioxide | 0.81 mg |

The active ingredients were suspended in Miglyol. Then the oil was mixed in a solution of methyl cellulose in water using an Ultra Turrax mixer for 5 min. The direct compression mixture was prepared by homogenizing the emulsion in a high shear mixer (Gral 10) with the microcrystalline cellulose Avicel PH-200. Admixing colloidal silicon dioxide was performed in a Turbula mixer during 10 minutes. Tablets weighing 65 mg were compressed on a Korsch PH 106 rotary press.

EXAMPLE 2

Mixtures based on microcrystalline cellulose with desogestrel and EE were prepared as described in example 1 applying emulsions with the following compositions (weight per tablet):

| | Composition applied emulsion (per tablet) in mg | | | | | | | | | | |
|---|---|---|---|---|---|---|---|---|---|---|---|
| | 1 | 2 | 3 | 4 | 5 | 6 | 7 | 8 | 9 | 10 | 11 |
| Miglyol 812 | 1.30 | 1.30 | — | — | — | — | — | — | — | 1.30 | — |
| Arachis oil | — | — | 1.30 | 1.30 | 1.30 | — | — | — | — | — | 1.30 |
| Sesame oil | — | — | — | — | — | 1.30 | 1.30 | 1.30 | 1.30 | — | — |
| CNC-sodium | 0.04 | — | 0.04 | — | — | 0.04 | — | — | — | — | — |
| Methylcell. MHB-50 | — | — | — | 0.07 | — | — | 0.07 | — | — | — | — |
| Span 80 | — | 0.13 | — | — | 0.13 | — | — | 0.13 | — | — | — |
| Tween 80 | — | 0.13 | — | — | 0.13 | — | — | 0.13 | — | — | — |
| Arabic gum | — | — | — | — | — | — | — | — | 0.2 | 0.2 | 0.2 |
| Water | 3.66 | 3.46 | 3.68 | 3.66 | 3.46 | 3.68 | 3.66 | 3.46 | 3.53 | 3.53 | 3.53 |

After admixing with colloidal silicon dioxide the mixture is compressed to tablets.

EXAMPLE 3

The active ingredient was processed to a homogeneous mixture comprising (per tablet):

| | |
|---|---|
| Org OD-14 | 0.3 mg |
| Miglyol 812 | 1.3 mg |
| Avicel PH-200 | 63.4 mg |

The active compound Org OD-14 [(7α, 17α)-17-hydroxy-7-methyl-19-nor-17-pregn-5(10)-en-20-yn-3-one] was mixed with the oil. Then the oil was homogenized in the mass of microcrystalline cellulose using a Gral 10 High shear mixer. The final mixture was compressed to tablets with a weight of 65 mg.

EXAMPLE 4

Tablets were prepared according the process described in Example 1 and with the following composition:

| | |
|---|---|
| Org 30659 | 60 μg |
| EE | 20 μg |
| Miglyol 812 | 1.3 mg |
| Methylcell MHB-50 | 0.02 mg |
| Water | 1.20 mg |
| Avicel PH-200 | 61.75 mg |
| Silicon dioxide | 0,65 mg |

EXAMPLE 5

The active ingredients were processed to a homogeneous mixture (weight per tablet):

| | |
|---|---|
| desogestrel | 150 μg |
| Ethinyl estradiol (EE) | 30 μg |
| Hydroxypropyl cellulose (HPC) | 150 μg |
| Water | 4.95 mg |
| Primojel | 2.65 mg |
| Avicel PH-200 | 57.06 mg |

HPC was dissolved in the water to a 3% HPC-solution. The active ingredients were suspended in this solution using an Ultra Turrax mixer for 5 min. The direct compression mixture was prepared by homogenizing the desogestrel/EE suspension in a high shear mixer (Gral 10) with the microcrystalline cellulose Avicel PH-200 and Primojel. Tablets weighing 65 mg were compressed on a Korsch PH 106 rotary press.

EXAMPLE 6

The active ingredients were processed to a homogeneous mixture (weight per tablet):

| | |
|---|---|
| desogestrel | 150 μg |
| Ethinyl estradiol (EE) | 30 μg |
| Hydroxypropyl cellulose (HPC) | 150 μg |
| Gelucire 35/10 | 2.44 mg |

-continued

| | |
|---|---|
| Water | 2.44 mg |
| Sodium Laurylsulfate (SLS) | 0.32 mg |
| Avicel PH-200 | 58.67 mg |
| Silicon dioxide | 0.81 mg |

The Gelucire was heated at 50° C., after which the active ingredients were suspended. The mixture was mixed in a solution of HPC in water using an Ultra Turrax mixer for 5 min. The direct compression mixture was prepared by homogenizing the desogestrel/EE emulsion in a high shear mixer (Gral 10) with the microcrystalline cellulose Avicel PH-200 and SLS. Admixing colloidal silicon dioxide was performed in an Erweka mixer for 1 min. Tablets weighing 65 mg were compressed on a Korsch PH 106 rotary press.

EXAMPLE 7

Tablets were prepared according to the composition and the procedure as described in Example 1. The two batches of tablets comprised 150 μg of desogestrel (uncoated tablets) and 60 μg of Org 30659 (coated tablets) respectively. The tablets were subjected to accelerated storage conditions. The stability results are depicted in the Table (RH=relative humidity).

| | desogestrel (%) after 3 months of storage | Org 30659 (%) after 1 month of storage |
|---|---|---|
| 40° C./50% RH | — | 97.8 |
| 40° C./ambient | 98.9 | — |
| 40° C./75% RH | 100.0 | 97.3 |
| 50° C./75% RH | 100.4 | — |

The results indicate a good stability of both progestagens in tablets in accelerated storage conditions.

EXAMPLE 8

A composition comprising a water insoluble non-cross-linked polymeric excipient capable of binding water according to this invention (Avicel PH-200) was compared with a composition comprising a water insoluble non-cross-linked polymeric excipient capable of binding water having a mean particle size smaller than 150 μm (Avicel PH-102) and with a composition comprising a water insoluble cross-linked polymeric excipient capable of binding water according to EP 598,337 (crospovidone), each composition being with or without oil (miglyol): Compositions (amounts in g):

| composition | miglyol 812 | HPC* | water | Avicel PH-200 | total mass |
|---|---|---|---|---|---|
| A | 0 | 0.5 | 15.5 | 183.8 | 200 |
| B | 4.0 | 0.4 | 11.6 | 183.8 | 200 |
| composition | miglyol 812 | HPC* | water | Avicel PH-102 | total mass |
| C | 0 | 0.5 | 15.5 | 183.8 | 200 |
| D | 4.0 | 0.4 | 11.6 | 183.8 | 200 |
| composition | miglyol 812 | HPC* | water | Polyplasdone XL 10# | total mass |

-continued

|   |     |     |     |      |     |
|---|-----|-----|-----|------|-----|
| E | 0   | 0.2 | 7.8 | 92.0 | 100 |
| F | 2.0 | 0.2 | 5.8 | 92.0 | 100 |

*Hydroxy propyl cellulose
crospovidone

The flowability was determined by measuring the amount of composition in g per sec passing through a funnel, having a diameter of 9.0 mm. The compositions B, D, and F are an 8% emulsion (2% miglyol), the compositions A, C, and E are an 8% HPC solution:

| composition | flowability in g/s |
|---|---|
| A | 2.97 |
| B | 1.49 |
| C | 0 |
| D | 0 |
| E | 0 |
| F | 0 |

We claim:

1. A solid pharmaceutical composition comprising at least one solvent or dispersant selected from the group consisting of an oil, an oily substance, an aqueous dispersion of an oil or oily substance, and water, a low dosage active ingredient, and a water insoluble non-cross-linked polymeric excipient that binds water and has a particle size distribution wherein at least 50% of the particles by volume have a diameter of from $150\mu$ to $200\mu$, wherein the oil, oily substance or dispersion is present in an amount by which the oil or oily substance contributes from 0% to 7% by weight of the pharmaceutical composition and wherein any water present is present in an amount by which the weight ratio of polymeric excipient to water is greater than 5:1.

2. The solid pharmaceutical composition of claim 1, comprising from about 0.1% to 4% by weight of an oil or oily substance.

3. The solid pharmaceutical composition of claim 1 wherein the oil or oily substance has a melting point below about 40° C.

4. The solid pharmaceutical composition of claim 1, wherein the active ingredient comprises a dosage of 0.005 to 5 percent by weight.

5. The solid pharmaceutical composition of claim 1, wherein the active ingredient is a steroid.

6. The solid pharmaceutical composition of claim 1, wherein the water insoluble non-cross-linked polyermic excipient that binds water has a particle size distribution wherein no more than 10% of the particles by volume have a diameter of $70\mu$ or less, at least 50% of the particles by volume have a diameter of from $150\mu$ to $200\mu$, and 90% of the particles by volume have a diameter of $260\mu$ or less.

7. The solid pharmaceutical composition of claim 1, wherein the water insoluble non-cross-linked polymeric excipient that binds water is a cellulose or a starch.

8. The solid pharmaceutical composition of claim 1, wherein the active ingredient is selected from the group consisting of desogestrel, ethinyl estradiol and a mixture thereof.

9. A process for the preparation of the solid pharmaceutical composition of claim 1, comprising dissolving or dispersing a low dosage of an active ingredient in an oil or an oily substance, an aqueous dispersion thereof, or in water, and mixing the dissolved or dispersed active ingredient with a water insoluble non-cross-linked polymeric excipient that binds water and has a particle size distribution wherein at least 50% of the particles by volume have diameter of from $150\mu$ to $200\mu$.

10. The process according to claim 9, wherein the ratio of the water insoluble non-cross-linked polymeric excipient that binds water and water present in the process is greater than 5:1.

11. The process according to claim 10, wherein the ratio of the water insoluble non-cross-linked polymer excipient that binds water and water present in the process is greater than 10:1.

* * * * *